United States Patent [19]
Hatch

[11] 4,024,398
[45] May 17, 1977

[54] DATA DERANDOMIZER AND METHOD OF OPERATION FOR RADIATION IMAGING DETECTION SYSTEMS

[75] Inventor: Kenneth F. Hatch, Prospect, Conn.
[73] Assignee: Picker Corporation, Cleveland, Ohio
[22] Filed: May 12, 1975
[21] Appl. No.: 576,309

Related U.S. Application Data
[63] Continuation-in-part of Ser. No. 478,201, June 11, 1974, abandoned.
[52] U.S. Cl. .......................... 250/363 S; 250/366
[51] Int. Cl.² ........................................ G01T 1/20
[58] Field of Search ....... 250/363, 366, 367, 363 S; 307/230, 246; 328/99; 330/30 D

[56] References Cited
UNITED STATES PATENTS

| | | | |
|---|---|---|---|
| 3,061,671 | 10/1962 | Waller | 328/99 |
| 3,234,472 | 2/1966 | Ebeling et al. | 328/151 |
| 3,532,927 | 10/1970 | Hindel | 315/367 |
| 3,535,550 | 10/1970 | Kang | 307/230 |
| 3,551,703 | 2/1970 | Bischoff | 328/99 |
| 3,586,878 | 6/1971 | Maxham | 328/151 |
| 3,638,045 | 1/1972 | Hughes | 307/246 |
| 3,681,601 | 8/1972 | Paap | 328/151 |
| 3,752,988 | 8/1973 | Culver | 250/363 |
| 3,862,425 | 1/1975 | Myers | 250/363 S |
| 3,904,530 | 9/1975 | Martone et al. | 250/336 |

*Primary Examiner*—Harold A. Dixon
*Attorney, Agent, or Firm*—Watts, Hoffmann, Fisher & Heinke, Co.

[57] ABSTRACT

A nuclear imaging system includes an analog signal processor which features analog data derandomization for minimizing data loss due to pulse pile-up. A scintillation detector provides a sequence of analog data pulses to the signal processor, the data pulses characterizing the energy level and situs of respective radiation events striking the detector. The signal processor includes sets of novel peak detectors and of sample and hold circuits which are serially connected and are operated to derandomize or space the sequence of analog data pulses so that the system can process pulses corresponding to photopeak events occurring only 1.5 microseconds apart. The analog data pulses are stored in analog pulse form in the peak detectors and are selectively transferred into the sample and hold circuitry from which they are transferred to the display mechanism. The signal processor is multiplexed with several data input channels for accommodating dual isotope operation.

A control unit is provided which controls the data processing cycle according to a predetermined processing time, or according to signals from external system apparatus. The control unit provides automatic resetting for assurance that the signal processor does not become locked into an inoperative, nondata processing state. The novel peak detectors are controlled by the control unit and feature input biasing for increased detection sensitivity, proportional dumping for discharging the stored peak value at a rate proportional to the value of the stored peak, and selective input data gating so that only the peak containing portion of the input signal is input into the detector.

28 Claims, 10 Drawing Figures

DATA DERANDOMIZER AND METHOD OF OPERATION FOR RADIATION IMAGING DETECTION SYSTEMS

CROSS-REFERENCES TO RELATED PATENT APPLICATIONS AND PATENTS

This application is a continuation-in-part of U.S. Patent application entitled DATA DERANDOMIZER AND METHOD OF OPERATION FOR RADIATION IMAGING DETECTION SYSTEMS, Ser. No. 478,201, filed June 11, 1974, now abandoned.

BACKGROUND OF THE INVENTION

This invention pertains to the art of radiation imaging detection systems, and more particularly to clinical nuclear detection systems having analog data derandomizing circuitry for reducing data loss due to pulse pile-up.

In one method of diagnosing certain illnesses radioactive isotopes are administered to a patient under study. Particular isotopes are selected which concentrate in certain types of tissue, with the degree of concentration in the tissue being dependent on the type of tissue. For example, a greater portion of an administered quantity of Iodine 131 will collect or concentrate in the tissue of the thyroid gland than in surrounding tissue. The isotope emits an amount of gamma radiation proportional to its concentration, and the surrounding tissue absorbs a varying amount. Gamma radiation emitted from the tissue is detected and graphically presented as an image on a suitable readout device, such as a cathode ray device or a chart recorder. The image is a valuable aid in diagnosing the condition of the tissue under examination.

One well-known type of device developing an image of the distribution of a radioisotope is the scintillation camera. Scintillation cameras generally have a relatively large disc-shaped scintillation crystal which is positioned so that the crystal intercepts the gamma radiation emitted by the patient. The crystal scintillates upon absorbing gamma-ray energy and provides pulses of light energy. A thallium-activated sodium iodide crystal is conventionally employed as the scintillation crystal.

A plurality of phototubes are positioned near and optically coupled to the crystal so that a scintillation is normally detected by several of the phototubes. Each of the detecting phototubes develops an electrical signal having an amplitude proportional to the intensity of light received by it from a scintillation and the received intensity is a function of the brightness of scintillation and its distance from the phototube. The signals developed by the phototubes are amplified and applied to appropriate electronic computing circuitry which develops electrical data signals representative of the situs and the intensity of the scintillation. One such gamma radiation imaging camera system is disclosed in the above-referenced patent entitled SCINTILLATION DETECTOR INDICATING SYSTEM.

A major problem with previous radiation imaging detection system has been data loss due to the phenomena commonly referred to as pulse pile-up. Radiation emanating from a radioisotope intercepts the scintillation crystal generally at random time intervals. The probability of a pulse being generated in any time interval $t$ is given by the equation $P = 1 - e^{-\Delta t/\tau}$, where $\tau$ is the average period between pulses. Thus, several scintillation events may occur in the crystal in rapid succession, and then there may be a relatively long interval of time before a succeeding scintillation event occurs. When several scintillation events occur in rapid succession, the corresponding data signals are developed in rapid succession with a minimum of separation between the signals.

In the operation of previous analog imaging detection systems, if successive data signals are presented for display while a signal is being displayed, the successive data signals are irrestorably lost. Thus, data signals which are spaced in a sequence by a time interval less than the display or processing time, are aborted and forever lost.

Some prior art radiation imaging systems are digital systems which digitize the preamplified signals, as described in the above referred SYSTEM patent. An attempt to solve the pulse pile-up problem in the digital system is described in the above-referenced DATA DERANDOMIZER application. In this digital derandomizer, the incoming digital data is stored in a shift register until it can be accommodated by the display. This shift register method of derandomization has proven successful in digital systems.

Digital systems exhibit a relatively slow system operating rate compared to contemporary analog systems. For example, a typical minimum pulse separation of 3-5 microseconds may be required in digital derandomized systems. The radiation detection and front end data processor section of the system is common to both digital and analog systems, and is capable of generating data pulses separated by only one or two microseconds. Digitizing is time-consuming, and even derandomizing the digital signals accordingly will not provide the fastest operating system. Only analog systems have the capability to provide overall system operating speed commensurate with the radiation detection circuitry and the front end data processor section.

Although the described shift register method of derandomization has proven successful in digital systems, it is not suitable for analog systems. Analog systems require the stored data to retain their amplitudes in proportion to the intensity of the detected scintillation; whereas digital systems store the data as binary numbers. For this reason, analog systems require a method of derandomization which allows the retention of pulse height data.

The prior art has attempted to alleviate the pulse pile-up problem in nonclinical analog, gamma ray-scintillator systems used for spectral analysis of gamma radiation as opposed to the detection of and reconstruction of the situs of gamma radiation events of preselected energy values. In well-logging operations a scintillation detector and a fast neutron source are positioned within the earth, and the scintillation detector is pulsed by a clock coincidentally with pulsing of the neutron source. The neutron source produces pulses of gamma rays which pass through the geological structure and strike the detector to produce an array of data pulses. The pulses are transmitted over several miles of cable and tend to become distorted and to pile up by the time they reach the data processing system on the earth's is surface.

In an attempt to remedy this pile-up problem, the prior art has suggested a data processing system which is responsive to both the clock and the data pulses. The system is initially reset by each pulsing of the neutron source and is conditioned to receive a series of data pulses which would otherwise reach the surface with insufficient time separation for data processing. The pulses are selectively gated into a bank of parallel charge and hold storage circuits, and are sequentially discharged from the charge and hold circuits upon expiration of various preselected time periods.

This type of system which relies on an initial time reference signal is unacceptable for clinical nuclear scanning. In clinical nuclear scanning the data pulses occur more randomly and do not occur as a consequence of a prearranged event which may be utilized as a time reference signal for initializing the storage circuits.

BRIEF SUMMARY OF THE INVENTION

The present invention overcomes the above-noted and other disadvantages in providing a new and improved analog nuclear radiation imaging system which has an analog signal processor that derandomizes the analog data. Digitalization of the analog data pulses is not required, and by employing a novel peak detector circuit, an overall faster operation, more responsive system is provided. The signal processing circuitry accommodates dual isotope applications and is adapted to operate under internally generated control conditions or under externally generated control conditions.

According to one aspect of the present invention, a scintillation camera system includes a detector, signal processor which provides data derandomization, and a display system. The detector generates electrical pulses in response to photopeak events of gamma radiation occurring in its crystal. The detector and its associated circuitry produce a sequence of sets of data pulses representing $x+$, $x-$, $y+$, and $y-$ coordinate information of each photopeak event. Z energy data pulses are also provided which are indicative of the total energy of each of the photopeak events.

The signal processor receives the sets of coordinate and energy data pulses corresponding to a photopeak event and provides them in a form required for display. The data pulses generated in response to sequential photopeak events are derandomized or spaced as they are output from the signal processor. More specifically, as data pulses from a previous event are being processed in the display system, the signal processor temporarily stores the data pulses from subsequent events until the display system can accommodate it.

The signal processor is comprised of cascaded sets of pulse storage cells which include a set of five peak detectors, and a pair of sample and hold circuits. A pair of summing and ratio circuits and a control timing circuit are also provided. The set of peak detectors receives and stores the $x+$, $x-$, $y-$, $y+$ and Z energy data pulses. Input and output of the data pulses are controlled by the control timing circuit.

The pair of summing and ratio circuits are coupled to the output of the peak detectors. The summing and ratio circuits algebraically combine the $x+$ and $x-$ coordinate data pulses and the $y+$ and $y-$ coordinate data pulses and then normalizes each of these coordinate pulses with respect to the Z energy data.

The pair of sample and hold circuits are coupled to the summing ratio circuits for storing the normalized $x$ and $y$ coordinate data pulses. The sample and hold circuits have output terminals which hold the coordinate data pulses and which are connected to the display system. The data pulses are maintained on the output terminals for a time period sufficient for the display mechanism to produce the image.

The control timing circuit is provided for controlling the transfer of the data into the peak detectors and into the sample and hold circuits. If the sample and hold circuits have maintained output of the respective data pulses for a sufficient time, the control timing circuit generates a dump signal for dumping or erasing the maintained data pulses and generates a sample gate pulse for transferring new pulses from the peak detectors through the ratio circuits, and into the sample and hold circuitry. If the sample and hold circuits have not disposed of their data pulses, the peak detectors retain subsequent incoming pulses until the sample and hold circuitry disposes of its data pulses to the display system.

A feature of the control timing circuit is that it allows the signal processor to accommodate dual isotope operation. The control timing circuit conditions the processor to be responsive to a preselected one of the isotope data channels or to be responsive to both channels and to prefer a preselected channel for data processing.

Another feature of the control timing circuit is an emergency reset signal generator which automatically resets the control circuit after a predetermined period of time. This assures that the signal processor will not become set in an inoperative, nondata processing state.

Still another feature of the control timing circuit is an external input line which allows external control circuitry to control the signal processor. If additional derandomizing time is required beyond that provided by the internally controlled analog derandomizing circuitry, external circuitry, such as a digital derandomizer, may input an external control signal for interrupting and extending the data processing cycle. The external control signal maintains the output of the data pulse from the sample and hold circuits for the duration of the external signal.

Yet another feature of the invention is the novel peak detector circuit used in the signal processor. The peak detector includes a differential voltage detector, an input gate which selectively couples data to the voltage detector, an output circuit, a holding capacitor coupled between the voltage deetector and the output of the voltage detector, a feedback circuit for discharging the holding capacitor in response to the magnitude of the output voltage of the peak detector, and a pedestal input voltage circuit for automatically increasing the magnitude of the input pulse by a predetermined voltage increment.

The control timing circuit operates the input gate to allow only the peak containing portion of the analog data pulse to reach the voltage detector. By gating out the leading 0.5 microsecond portion of a subsequent data pulse, additional time is acquired for processing the previous data pulse.

The pedestal input voltage circuit effectively applies a selected increment of voltage bias to each input data pulse. The voltage bias facilitates pulse detection and fidelity of the output pulse reproduction by increasing the difference between the value of each received data signal and the value of a nondata input voltage. A predetermined amount of current is injected in the absence of a data pulse to bias the input of the voltage detector to a value which is substantially different from the value of the input signal in the absence of a data pulse. This allows the peak detector to be biased such that the voltage magnitude of each received data pulse lies within the linear range of operation of the peak detector.

An emitter-follower circuit is coupled to the output of the differential voltage detector for charging the holding capacitor rapidly. The proportional dumping circuit provides for rapid discharge of the holding capacitor by discharging it at a rate proportional to the output voltage. Both of these features provide an overall faster operating circuit.

It accordingly is an overall object of this invention to provide a novel and improved nuclear radiation detection system having analog data processing circuitry featuring analog data derandomization and high speed operation.

Other objects and advantages of the invention will become apparent from the following description of a preferred embodiment when read in conjunction with the accompanying drawings wherein.

DESCRIPTION OF THE PREFERRED EMBODIMENT

Figure 1:
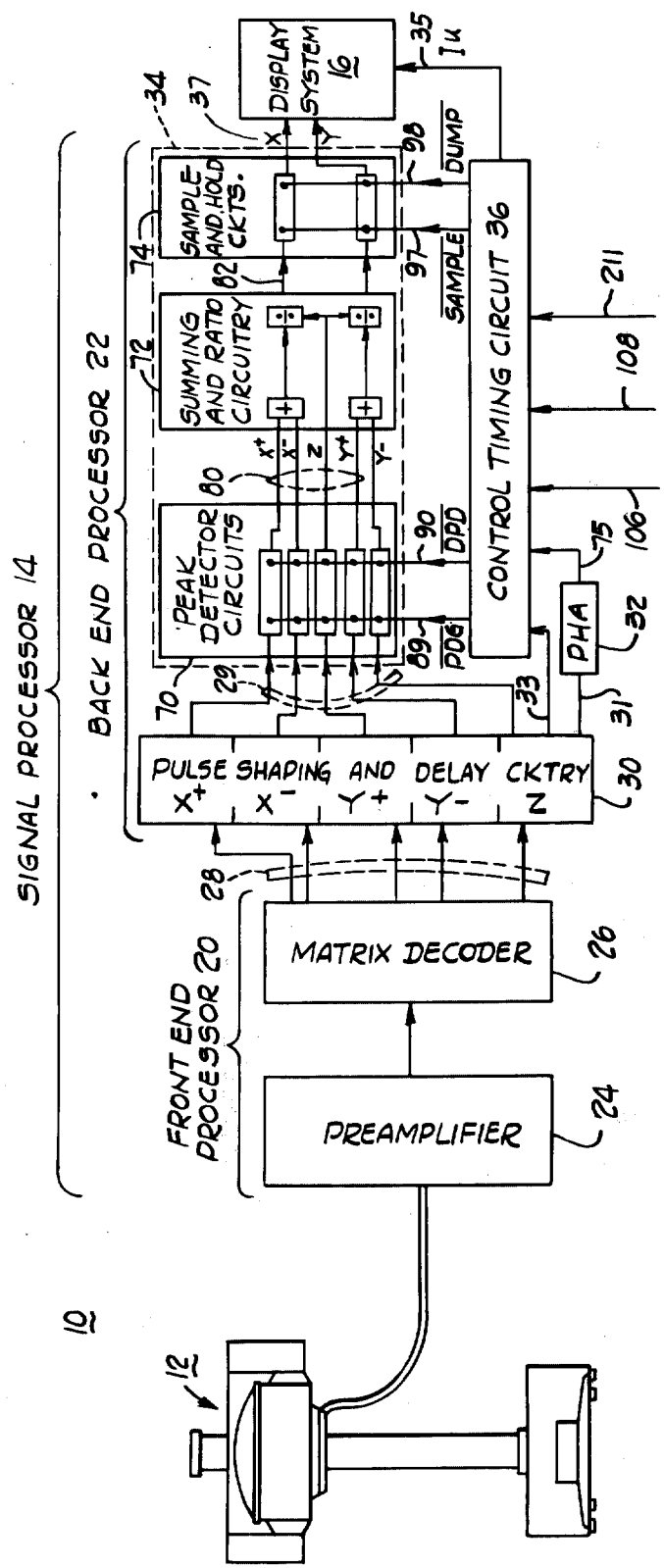
FIG. 1 is a block diagram of a nuclear radiation imaging system having data processing circuitry featuring analog data derandomization in accordance with one embodiment of the invention.

A nuclear radiation imaging system for clinically examining a body is shown schematically at 10 in FIG. 1. The imaging system 10 generally includes a scintillation camera system 12, a signal processor 14, and a display system 16. The scintillation camera system 12 is positioned adjacent the body (not shown) which has previously been administered a radioisotope. The system 12 produces a sequence of electrical event pulse signals indicative of the radiation being emitted from the body. The signal processor 14 converts the electrical signals into data which characterizes the situs and strength of the radiation as it is emitted from the body. The strength and situs data is input to the display system 16 for producing a visual profile of the radiation as it emerges from the body. The profile is a valuable diagnostic aid in examining the internal structure of the body.

The scintillation camera system 12 includes a scintillator crystal and a collimator. The collimator absorbs unwanted radiation emitted from the body so that radiation from determinable spatial origins passes onto the scintillator crystal and causes scintillations. A plurality of phototubes are positioned near and optically coupled to the scintillator crystal for detecting the scintillations and producing the series of electrical signals. In the disclosed embodiment there are nineteen phototubes, and they provide nineteen channels of analog data signals whose values are representative of the strength and location of the scintillations.

The signal processor 14 converts the nineteen channels of analog data signals into $x$ coordinate analog data, $y$ coordinate analog data and into Z energy analog data. The signal processor 14 includes a front end processor 20 and a back end processor 22. The front end processor 20 includes a preamplifier section 24 for amplifying the nineteen channels of data and a decoder 26. The decoder 26 comprises five matrices which selectively combines the 19 channels of data to provide $x+$, $x-$, $y+$, $y-$ coordinate analog data signals and a Z energy analog data signal. The coordinate data signals characterize the situs of an individual scintillation, and the Z energy signal characterizes the intensity of the individual scintillation. A set of five lines 28 couple to coordinate and energy data to the back end processor 22.

As described, the scintillation camera system 12, the signal processor 14 including the front end processor 20, and the display system 16 are now conventional. Their operation is well known in the art, and further description is unneeded. A more detailed description of the system 12 is found in the referenced SUBASSEMBLY patent, and an additional description of a signal processor as it actuates a display is found in the referenced INDICATING SYSTEM patent.

The back end processor 22 is constructed and arranged according to the invention to derandomize and provide the coordinate and energy analog data for display on the display system 16. The back end processor 22 includes pulse-shaping and delay circuitry 30, a pulse-height analyzer 32, signal processing circuitry 34, a control timing circuit 36. The pulse-shaping and delay circuitry 30 shapes and delays the coordinate and energy data on the lines 28 for causing coincidence of all data corresponding to a specific scintillation. The energy and coordinate analog data signals are input via a set of lines 29 into the signal processing circuitry 34 where they are converted into output analog data indicative of the situs and strength of the scintillation. A Z energy channel signal (referred to as the pulse present, PP signal) is coupled from the circuitry 30 to the control timing circuit 36 by a line 33. The pulse present PP signal is indicative of the occurrences of a valid data pulse on the lines 29.

The pulse-height detector 32 and the control timing circuit 36 control input and output data operation of the signal processing circuitry 34 to provide derandomization of the analog data for minimizing data loss due to pulse pile-up.

The pulse-height detector 32 is responsive to the Z energy analog data signal via a line 31 for measuring the total energy of the scintillation. If the value of the energy signal falls within a preselected range, a photopeak scintillation of interest has occurred and the detector 32 generates a PHA signal indicating this occurrence. The pulse-height detector is explained in detail in the referenced PULSE HEIGHT ANALYZER patent.

The signal processing circuitry 34 includes sets of cascaded storage cells which provide $x$ and $y$ analog data pulses to the display mechanism 16 on a set of lines 37. The control timing circuit 36 provides an unblank signal into the display mechanism 16 via a line 35 to allow display of the x and y data pulses. The x and y analog data pulses are maintained on the lines 37 for a period of at least three microseconds during which the unblank signal is produced. The unblank signal is typically provided for only 1.75 microseconds of the three microsecond period to assure display accuracy.

Figure 2:
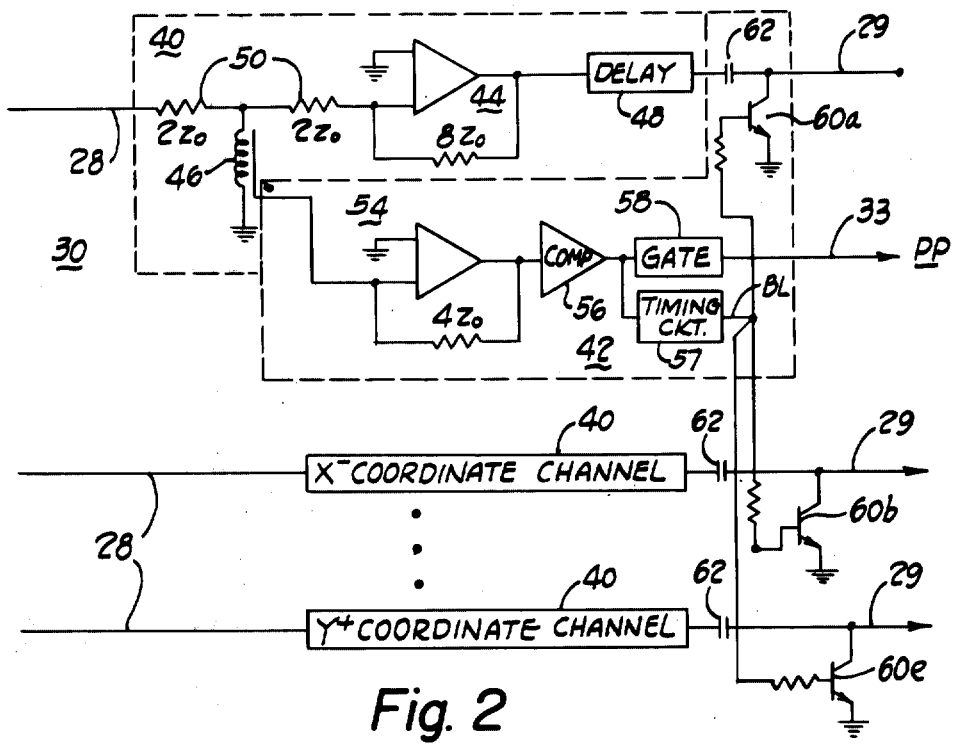
FIG. 2 is a circuit schematic of a clipping circuit used in the system of FIG. 1.

The pulse-shaping and delay circuitry 30 is shown in detail in FIG. 2. The circuitry 30 includes five channels of single chip and delay circuitry 40 and one double chip channel 42. The delay circuitry 40 is coupled to the lines 28 for receiving the x+, x−, y+, y− and Z energy pulses. The five channels 40 convert the data and energy pulses into signal delay line clipped waveforms. The channel 42 is coupled to the Z energy channel and converts the energy pulses into a double delay line clipped pulse to provide the pulse present PP pulse and baseline restorer pulse BL.

Each channel 40 is comprised of an operational amplifier arrangement 44, and a pair of delay lines 46, 48. A pair of resistors 50 ar serially interconnected to one input of the amplifier arrangement 44 and to the line 28 to serve as an input to the channel 40. The delay line 46 commonly couples the resistors 50 to circuit ground and causes the output of the amplifier arrangement 44 to produce the single delay line clipped waveform. The delay line 48 is coupled to the output of the amplifier arrangement 44 to provide a timing delay to the single delay line clipped waveform.

The double clip channel 42 is comprised of an amplifier arrangement 54 which has one input coupled to the shield of the delay line 46. A comparator 56 and a logic gate 58 are serially connected to the output to the amplifier arrangement 54. The signal produced by the logic gate 58 is the double delay line clip generated pulse present PP waveform on the line 33. A timing circuit 57 is also coupled to comparator 56 to generate baseline restoring pulses, BL, for the bases of transistors 60 a through 60e.

A set of restoring transistors 60a–60e and a set of coupling capacitors 62 are coupled to the respective outputs of the delay lines 48 in each of the five channels 40. The coupling capacitor 62 removes high speed A.C. base line fluctuations in each channel. The restoring transistor 60a has its base terminal commonly connected to the timing circuit 57, and has its collector-emitter path coupling the capacitor 62 to circuit ground. The transistor 60a is rendered nonconductive upon the occurrence of a pulse present PP pulse. This allows charging of the capacitor 62 for stabilizing the base line of pulses from the output of the delay line 48.

The value of the delay line 48 is chosen so that the baseline restoring pulse BL is earlier than the single delay line waveform when each reaches the restoring transistor 60.

Operation of the pulse-shaping and delay circuitry 30 is as follows. The x+, x−, y+, y−, and Z energy pulses are input into the respective clipping and delay circuits 40. Each clipping and delay circuit 40 produces a single delay line clipped data pulse, which is time coincident with a double delay line clipped data pulse, PP, produced by the channel 42. The respective PP pulses render the restoring transistors nonconductive, allowing the data pulses to propagate to the signal processing circuitry 34. Absent the PP pulse, the restoring transistors are conductive and the respective capacitors C are coupled to the circuit ground, allowing the capacitors C to change in preparation for the next data pulse. A more detailed description of the circuits 40, 42 is found in the referenced DELAY LINE CLIPPING patent application.

As shown in FIG. 1, the signal processing circuitry 34 is comprised of a set of five peak detectors 70, a pair of two summing and ratio circuits 72 coupled to the outputs of the peak detector circuits 70, and a pair of sample and hold circuits 74 coupled to the output of the summing and ratio circuits 72. The control timing circuit 36 is coupled for controlling operation of the peak detectors 70, of the sample and hold circuits 74 and of the display mechanism 16.

The control of timing circuit 36 is responsive to the double delay line clipped PP pulse on the line 33 from the shaping and delay circuitry 30 to the output from the pulse-height detector 32 via a line 75, and to a pair of operator supplied inputs 106, 108. The control time circuit 36 selectively generates a peak detector gating pulse (the $\overline{PDG}$ pulse) to allow data to be gated into the peak detectors 70. The circuit 36 generates a peak detector dump signal (hereafter the $\overline{DPD}$ signal) for discharging the output of the peak detectors 70 in preparation for a new peak detector output. In addition, the control timing circuit 36 generates a sample gate signal (hereafter the $\overline{SAMPLE}$ signal) to gate data pulses into the sample and hold circuit 74. Further, the circuit 36 generates a sample dump signal (hereafter the $\overline{DUMP}$ signal) for discharging the output of the sample and hold circuits 74 in preparation for a new output data pulse being supplied to the display system 16.

The peak detector circuits 70 have their respective inputs coupled to receive the x+, x=, y+, y−, and Z data on the lines 29. Upon a PDG gating signal from the circuit 36, the peaks of the respective data signals are input into the detectors 70. The peaks are stored in the detectors 70 for generating an output signal indicative of the stored peak on a set of output lines 80.

The summing and ratio circuits 72 are conventional and commercially available under the description AD 429, AD518 marketed by Analog Devices, Inc. The circuits 72 algebraically sum the x-coordinate data and the y-coordinate data provided on the line 80 and then divides the respective sums by the Z energy data to provide normalized x-coordinate and y-coordinate data. The normalized x-coordinate data and the normalized y-coordinate data and the energy data is then coupled via a set of lines 82 to the sample and hold circuits 74.

The sample and hold circuits 74 are of any conventional type having an input gating terminal to allow data sampling and having an output gate for discharging the stored data which had been sampled. A device which is suitable for use as a sample and hold circuit is commercially available as a SHA 2a circuit, marketed by Analog Devices, Inc.

Upon a $\overline{SAMPLE}$ pulse from the control timing circuit 36, the normalized coordinate data are read into the respective sample and hold circuits 74. The sample and hold circuits provide an output indicative of the normalized data on the line 82 to the display system 16. The normalized coordinate data is maintained on the lines 37 for a predetermined period of time, usually three microseconds, sufficient for the display system to process and display the data. While the data is being presented on the lines 37, the timing circuit 36 provides the IU unblank pulse on the line 35 for unblanking the display. At the end of the predetermined period of time, the IU pulse has ended, and the control logic generates the $\overline{\text{DUMP}}$ pulse for erasing the data on the lines 33.

The derandomizing feature according to this invention is provided by the control timing circuit 36 when a subsequent set of data pulses is communicated as an input to the peak detectors 70 while the normalized data is still being maintained on the lines 37. Upon this condition the control timing circuit 36 generates a $\overline{\text{PDG}}$ signal but defers the $\overline{\text{SAMPLE}}$ pulse and the $\overline{\text{DUMP}}$ pulse until after the predetermined period of time has expired and until the $\overline{\text{DUMP}}$ pulse has discharged the normalized data from the lines 83. During this time the peak detectors 70 have input and stored the coordinate and energy data by generating the $\overline{\text{PDG}}$ and $\overline{\text{DPD}}$ signals, but the data is not gated into the sample and hold circuits 74 until after the occurrence of a $\overline{\text{DUMP}}$ pulse.

Figure 3:
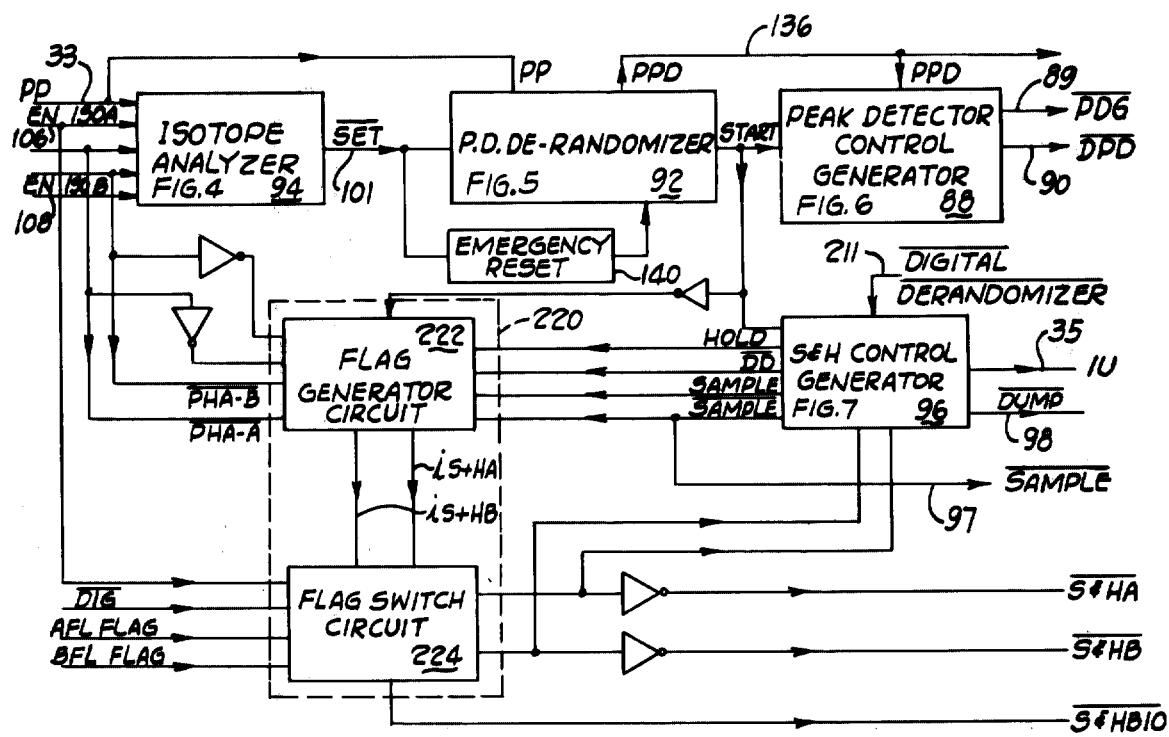
FIG. 3 is a schematic diagram of a control timing circuit utilized in the system of FIG. 1.

The above-operational sequence is more clearly understood when referring to FIG. 3 which shows the control timing circuit 36 in detail.

THE CONTROL TIMING CIRCUIT 36

The control timing circuit 36 comprises timing and logic circuitry which is responsive to the pulse present PP signal and to the PHA signal for generating the peak detector gating $\overline{\text{PDG}}$ and peak detector dump $\overline{\text{DPD}}$ signals. These signals control operation of the peak detectors 70. The circuit 36 generates the $\overline{\text{SAMPLE}}$ signal and the $\overline{\text{DUMP}}$ signal for controlling data pulse input and output in the sample and hold circuits 74.

The control timing circuit 36 is comprised of a peak detector control generator circuit 88, a peak detector derandomizer circuit 92, an isotope analyzer circuit 94 and a sample and hold control generator 96. The peak detector control generator circuit 88, 90 generates the $\overline{\text{PDG}}$ signal and the $\overline{\text{DPD}}$ signal to the peak detector 70. The peak detector derandomizer circuit 92 generates a START signal and a pulse present delayed PPD control signal to the peak detector control generator 88. The isotope analyzer circuit 94 generates a SET control signal to the derandomizer circuit 92 in response to the pulse present PP signal and to the PHA energy signals from the pulse-height analyzer circuit 32. The sample and hold control generator 96 generates the internal unblank IU pulse on the line 35 to the display system 16, and generates the $\overline{\text{DUMP}}$ and $\overline{\text{SAMPLE}}$ control signals respectively on a set of lines 98, 97 to the sample and hold circuits 74.

Figure 4:
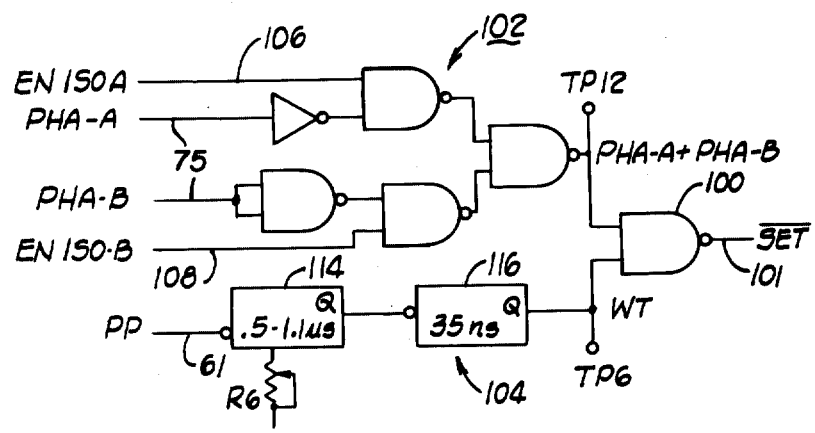
FIG. 4 is a circuit diagram of an isotope analyzer circuit utilized in the control circuit of FIG. 3.

Referring to FIG. 4, the isotope analyzer circuit 94 generates the SET timing signal on a line 101 to the derandomizer circuit 92 a predetermined time delay after the occurrence of a pulse present PP pulse. The analyzer circuit 94 is comprised of a gate 100 which produces the SET signal in response to logic circuitry 102 connected to one of its inputs and to timing circuitry 104 connected to the other of its inputs.

The logic circuitry 102 comprises a plurality of gates interconnected to provide a logic OR function. Operator-specified control signals, ENABLE ISOTOPE A, ENABLE ISOTOPE B, are input on the set of control lines 106, 108 to the logic circuitry 102. The PHA energy signals from the pulse-height analyzer 32 are coupled as inputs to the logic circuitry 102 on a set of lines 110, 112. The occurrence of a PHA energy signal causes the logic circuitry 102 to produce a signal to the gate 100 indicative of a photopeak event satisfying the energy conditions of the pulse-height analyzer circuit 32.

For covenience of description, a single isotope system will be assumed. This assumption facilitates understanding of the overall operation of the system. It will be understood, however, that dual isotope operation is a preferred embodiment, which will be further described with respect to FIG. 10.

The timing circuitry 104 comprises a pair of serially connected one-shot generator circuits 114, 116. The pulse present PP pulse is input to the first one-shot generator circuit 114 which is adjusted to provide an output pulse having a duration of approximately one microsecond. The one microsecond time period causes a delay before generation of the SET timing signal so that the SET signal is generated approximately 100 nanoseconds after the peak of the single delay line clipped pulse input to PHA 32. This time is approximately coincident with that of the peaks from the single delay line clip data pulses received from the pulse-shaping and delay circuitry 30. The one-shot generator circuit 116 is actuated at the end of the one microsecond pulse from the one-shot circuit 114 and generates a pulse having a pulse width of approximately 35 nanoseconds to the gate 100. Upon the simultaneous occurrence of a signal from the logic circuitry 102 and an output pulse from the one-shot circuit 116, the SET timing signal is generated.

Figure 5:
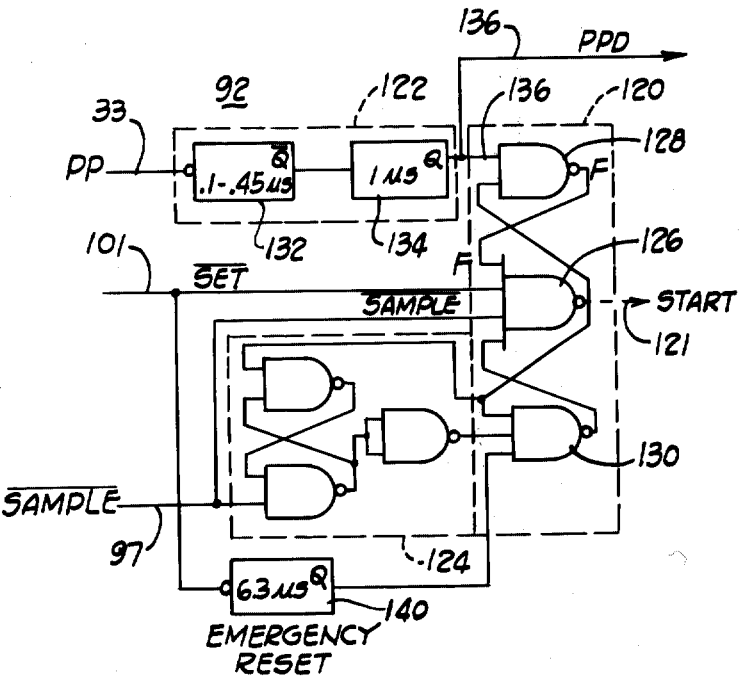
FIG. 5 is a circuit diagram of a peak detector derandomizer circuit used in the control circuit of FIG. 3.

Referring to FIG. 5, the peak detector derandomizer circuit 92 is responsive to the SET timing pulse on the line 101 from the isotope analyzer circuit 94 and to the pulse present PP pulse on the line 33 to generate the delayed pulse present PPD pulse and the START pulse S.

The peak detector derandomizer circuit 92 includes a three-gate latch arrangement 120 which produces the START signal. A timing generator circuit 122 and a latch circuit 124 are coupled to provide inputs to the latch arrangement 120.

The latch arrangement 120 comprises a start gate 126 connected in a latching arrangement with a pair of gates 128, 130. The start gate 126 is responsive to the SET signal on the line 101 and to the $\overline{\text{SAMPLE}}$ signal on the line 97. The gate 128 has an input connected to the timing generator circuit 122, and the gate 130 has an input connected to the latch circuit 124.

The timing generator circuit 122 comprises a pair of serially connected one-shot generator circuits 132, 134 which are responsive to the pulse present PP signal on the line 33. The one-shot generator circuits 132, 134 are an important feature of this invention as they produce the pulse present delay signal PPD, on a line 136 which is substantially coincident with the peak of the various data pulses as they are communicated to the peak detectors 70. The one-shot generator circuit 132 produces an approximate 0.5 microsecond pulse which provides a delay corresponding to the first 0.5 microseconds of the data pulse as it is coupled to the peak detectors 70. The one-shot generator circuit 134 produces the PPD pulse having a one microsecond width and the PPD pulse is input to the gate 128 for conditioning the start gate 126.

The latch circuit 124 is responsive to the $\overline{\text{SAMPLE}}$ signal on the line 97 and to the START signal on the start line 121. As soon as a START signal is generated by the gate 126, the gate 130 is latched into a logic zero state. The latch 124 is set into a logic 1 state which maintains the logic zero state of the gate 130 until the occurrence of a $\overline{\text{SAMPLE}}$ signal on the line 97. Because the peak detector control generator 88 is responsive to the START signal falling from a logic 1 to a logic zero to generate the peak detector gate signal $\overline{\text{PDG}}$, the latch 124 and the gate 130 function to prevent data from entering the peak detectors 70 until the occurrence of a $\overline{\text{SAMPLE}}$ signal. The $\overline{\text{SAMPLE}}$ signal on the line 97 resets the latch 124 and the gate 126, conditioning them for a subsequent set of data pulses.

If for any reason the $\overline{\text{SAMPLE}}$ signal was not generated on the line 97, the peak detector derandomizer circuit 92 would be effectively disabled. This would cause the signal processing circuitry 34 to be locked in an inoperative, nondata processing state. For overcoming this contingency, an emergency reset one-shot generator circuit 140 is provided as one feature of the invention. The one-shot generator circuit 140 is responsive to the $\overline{\text{SET}}$ signal on the line 101 and generate a logic one pulse Q having a duration of approximately six microseconds. If the gate 130 has not been reset at the expiration of the six microsecond period, the pulse Q returns to a logic zero state and causes the gate 130 to reset the start gate 126. This allows the next set of data to be processed.

Figure 6:
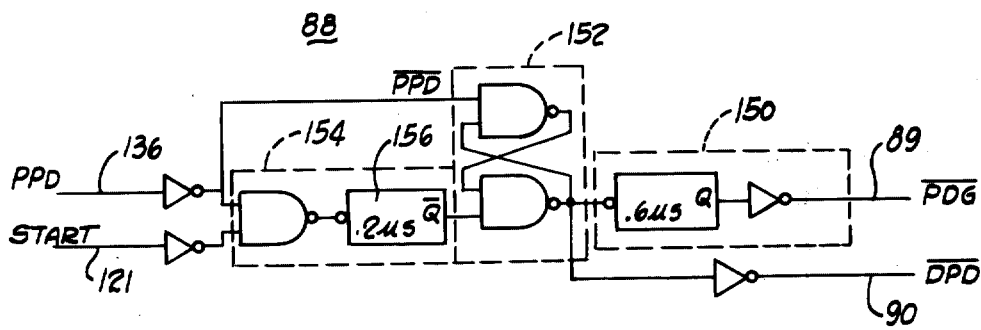
FIG. 6 is a circuit diagram of a peak detector control generator circuit utilized in the control circuit of FIG. 3.

The peak detector control generator 88 is shown in detail in FIG. 6. The control generator 88 is comprised of a gating one-shot circuit 150 which generates the $\overline{\text{PDG}}$ signal, a latch circuit 152 coupled to the gating one-shot circuit 150 and providing the dump peak detector $\overline{\text{DPD}}$ signal, and a timing one-shot circuit 154. The timing one-shot circuit 154 is responsive to the PPD signal on the line 136 from the output of the one-shot generator circuit 134 and to the START signal on the line 121 from the three gate latch arrangement 120.

Upon the occurrence of a pulse present delay PPD signal, the latch 152 is set into a logic state which actuates the gating one-shot circuit 150. The gating one-shot circuit 150 includes a signal generator for producing the peak detector gate $\overline{\text{PDG}}$ signal having a duration of approximately 0.6 microseconds on the line 89.

The setting of the latch circuit 152 also generates the peak detector dump $\overline{\text{DPD}}$ signal on the line 90. The peak detector dump $\overline{\text{DPD}}$ signal on the line 90 is maintained in a logic one state for enabling data to be transferred into the summing and ratio circuits 72 until the latch 152 is reset.

The latch 152 is reset upon the expiration of the pulse present delayed PPD signal and upon the START signal going to a logic zero state, indicating that a $\overline{\text{SAMPLE}}$ pulse has occurred at the gate 126 and that a new set of data is to be transferred into the sample and hold circuits 74. This causes the $\overline{\text{DPD}}$ signal to return to a logic zero state which dumps the peak detector, nulling the data signal on the lines 80. At this time new data has entered the sample and hold circuits 74.

When the START signal and the pulse present delayed PPD signal return to a logic zero, the one-shot generator 156 is triggered which immediately resets the latch 152 and holds it in a reset state for a period of approximately 0.25 microseconds. By holding the latch 152 in a reset state, it is assured that there is at least a 0.25 microsecond separation between dump peak detector $\overline{\text{DPD}}$ pulses even though another pulse present delayed PPD pulse has occurrred.

If a second pulse occurs to immediately force the PPD signal into a high state, the expiration of the START pulse will actuate the timing one-shot circuit 156. This is the result of the latch 124 causing the START signal to remain in a high state even though the pulse present delay PPD signal has returned to a low state.

Figure 7:
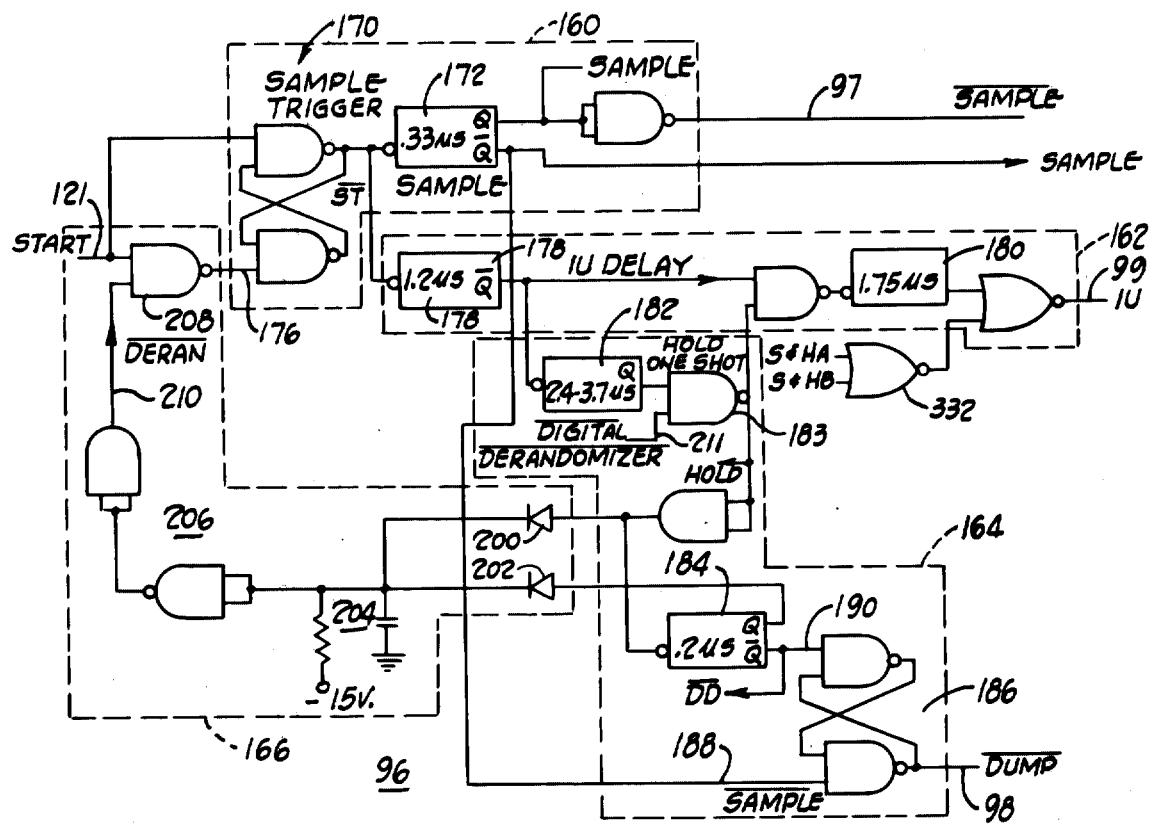
FIG. 7 is a circuit diagram of the sample and hold control generator circuit utilized in the control circuit of FIG. 3.

Referring to FIG. 7, the sample and hold control generator 96 is comprised of a sample generator circuit 160, an internal unblank generator circuit 162, a dump generator circuit 164, and a logic circuit 166. The sample generator circuit 160 is coupled to the peak detector derandomizer circuit 92 for receiving the START signal and generating the $\overline{\text{SAMPLE}}$ signal on the line 97. The circuit 160 is also coupled to provide inputs to the internal unblank generator circuit 162 and to the dump generator circuit 164. The logic circuit 166 couples signals from the generator circuits 162, 164 as inputs to the sample generator circuit 160.

The sample generator circuit 160 comprises a latch circuit 170 and a sample one-shot generator 172 which is adjusted to provide 0.33 microsecond pulses. The latch circuit 170 is responsive to the START signal on the input line 121 and is selectively latched into a logic state for producing a sample trigger, ST, signal. The ST signal actuates the sample one-shot generator 172 to generate the $\overline{\text{SAMPLE}}$ pulse on the line 97. The latch circuit 170 has another input line 176 coupled to the logic circuit 166 for selectively inhibiting the START signal on the line 121 from setting the latch circuit 170.

The internal unblank generator circuit 162 comprises delay and unblank one-shot generator circuits 178, 180, respectively. The delay one-shot generator circuit 178 is coupled to the latch circuit 170 and provides an internal unblank delay IUD signal which actuates the unblank one-shot generator circuit 180 after a 1.2 microsecond delay. The unblank one-shot generator circuit 180 produces the internal unblank IU signal having a pulse width of approximately 1.75 microseconds on the line 35.

The dump generator circuit 164 is comprised of a hold one-shot generator circuit 182, a delay one-shot generator circuit 184, and an output latch circuit 186. The output latch circuit 186 has an input line 188 coupled to receive the $\overline{\text{SAMPLE}}$ signal which sets the output latch circuit 186 to provide the $\overline{\text{DUMP}}$ signal on the line 98. The hold one-shot generator circuit 182 is coupled to the output of the delay one-shot generator circuit 178 and is actuated substantially simultaneously with the generation of the $\overline{\text{SAMPLE}}$ signal. The hold one-shot generator circuit 182 provides an approximate three microsecond HOLD pulse which is input to the logic circuit 166 and which actuates the delay one-shot generator circuit 184. At the expiration of the 3 microsecond HOLD pulse, the delay one-shot generator circuit 184 provides a 0.2 microsecond dump delay $\overline{\text{DD}}$ pulse which resets the output latch circuit 186 for removing the $\overline{\text{DUMP}}$ pulse. The 0.2 microsecond $\overline{\text{DD}}$ pulse causes the output latch circuit 186 to remain latched for the 0.2 microseconds to provide a minimum delay time between $\overline{\text{DUMP}}$ pulses on the line 98.

The logic circuit 166 comprises a pair of diodes 200, 202, an R.C. time-constant circuit 204, a pair of serially connected gates 206, and a derandomizer gate 208. The derandomizer gate 208 has one input connected to receive the START signal on the line 121 and has another input line 210 coupled to the gates 206. The gates 206 are serially connected and their input is coupled through the R.C. time-constant circuit 204 to the diodes 200, 202. The diode 200 is coupled to be actuated by the 3 microsecond HOLD pulse from the hold one-shot generator circuit 182. The diode 202 is connected to the output of the delay one-shot generator circuit 184 and is actuated upon generation of the 0.25 microsecond reset pulse.

The derandomizer gate 208 functions to maintain the latch circuit 170 in its set state after it has been set by the START pulse. The derandomizer gate 208 holds the latch circuit 170 in this state for the duration of the three microsecond HOLD pulse of the hold one-shot generator circuit 182 and during the 0.2 microseconds of the pulse from the delay one-shot generator circuit 184 as coupled through the diodes 200, 202, respectively. This serves to prevent subsequent START pulses on the line 121 from triggering a new set of $\overline{\text{SAMPLE}}$ and $\overline{\text{DUMP}}$ pulses for a period of at least 3.25 microseconds. This insures that data is present to the display system 16 for the 1.75 microsecond internal unblank IU period and for a subsequent period thereafter to guarantee complete display of the data. This is especially useful when the display system 16 is comprised of a storage scope, as the extra time is need to insure data is present while the dot on the scope is being removed.

EXTERNAL CONTROL

A feature of the present invention is the ability of this analog derandomizer system to interface with control equipment external to the control timing circuit 36, such as with a digital derandomizer circuit. Because digital data processing circuits typically require longer than a 3 microsecond data processing time, the dump generator circuit 164 has an external input line 211 for input of, for example, digital derandomizer flag signal. The derandomizer flag signal is input ont he derandomizer line 211 to a gate 183 coupled to the output of the hold one-shot generator 182. The flag signal functons to maintain the capacitor of the R.C. time constant circuit 204 charged after the expiration of the 3.0 microsecond HOLD pulse through the diode 200. This maintains the latch circuit 170 in its set state via derandomizer gate 208.

Figure 8:
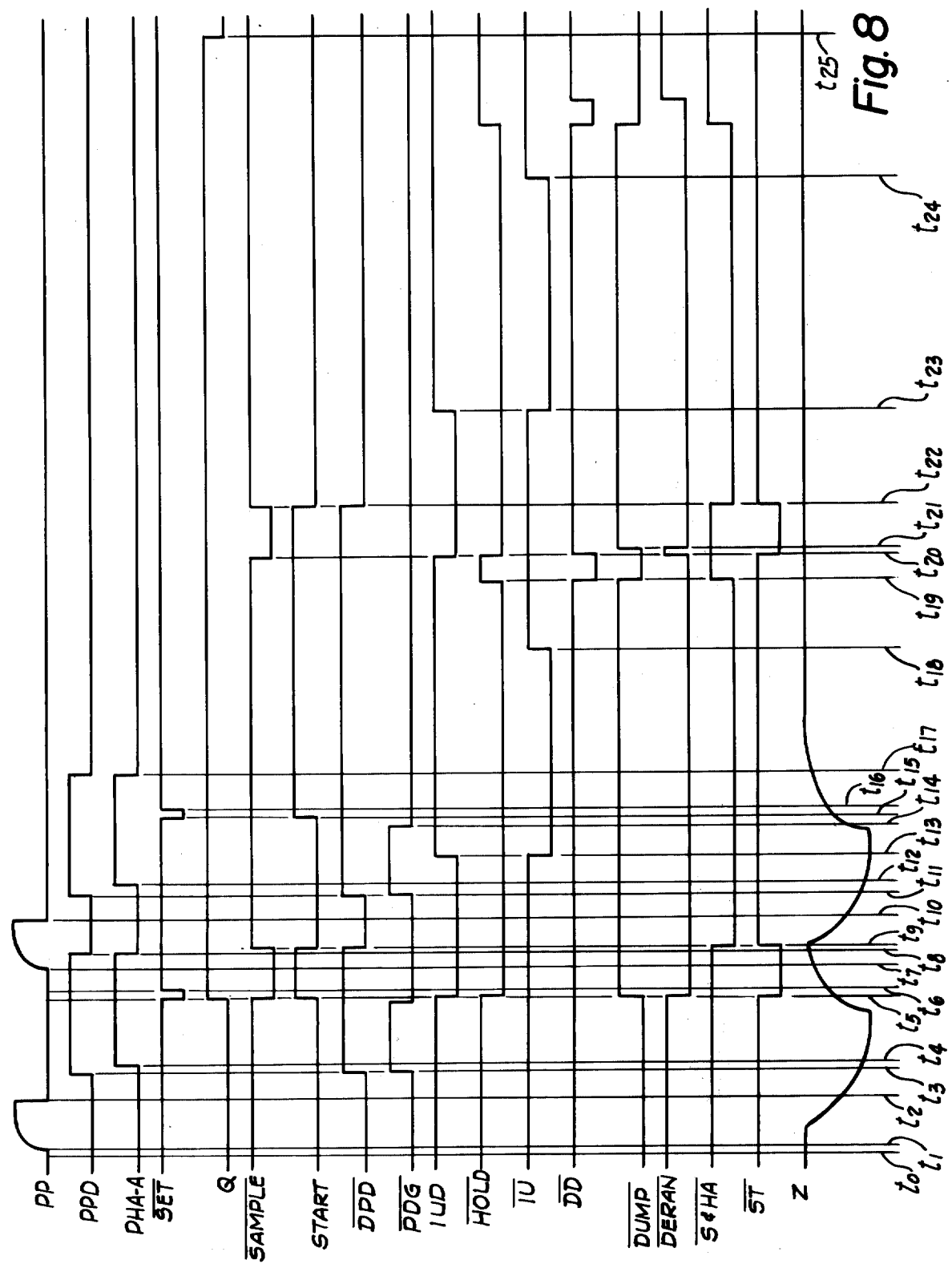
FIG. 8 is a set of exemplary waveforms which illustrate data derandomizing operation of the signal processor shown in FIG. 1.

Operation of the isotope analyzer circuit 94, the peak detector derandomizer circuit 92, the peak detector control generator 88, and the sample and hold control generator 96 is best understood when referring to the timing waveforms shown in the diagram of FIG. 8. The diagram is divided into periods t0–t23 and illustrates circuit functioning when two data pulses occur within a three microsecond period, thereby calling the derandomizing feature into operation.

Time t0 corresponds to circuit inactivation wherein there have been no pulses received from the front end processor 20 for a period of at least 7 microseconds. At time t1 a pulse present PP pulse is generated by the pulse-shaping and delay circuitry indicating that data pulses have been detected. The PP pulse is coupled on the line 33 to the timing circuitry 104 and to the timing generator circuit 122 respectively in the isotope analyzer 94 and in the peak detector derandomizer 92. At time t2 the pulse present PP pulse returns to a logic 0 state. At time t3 the pulse present delayed PPD pulse is initiated by the one-shot generator circuit 134, and the PPD pulse sets the latch circuit 152. This generates the 0.6 microsecond peak detector gate $\overline{\text{PDG}}$ pulse and the dump peak detector pulse $\overline{\text{DPD}}$ of indeterminant duration respectively on the lines 89 and 90.

The pulse present delayed PPD signal conditions the three gate latch arrangement 120 for producing the START signal on the line 121 upon the occurrence of the $\overline{\text{SET}}$ pulse.

Assuming a pulse has occurred in the A isotope system, a signal on the line 106 conditions the gate 100 to produce the $\overline{\text{SET}}$ signal approximately one microsecond from the falling edge of the pulse present PP signal. This timing places the $\overline{\text{SET}}$ pulse approximately 100 nanoseconds after the peaks of the respective data pulses.

At time t4 the PHA pulse occurs indicating the recognition by the pulse-height analyzer 32 of an energy pulse having an energy level exceeding a predetermined minimum. The PHA pulse conditions the gate 100 for generating the logic 0 $\overline{\text{SET}}$ signal at time t5 approximately one microsecond after the pulse present PP pulse returns to a logic 0. Immediately prior to time t5, the 0.6 microsecond $\overline{\text{PDG}}$ pulse times out. If the energy pulse has not exceeded an upper level set by the PHA at time t5, the gate 100 will remain enabled, and a WT pulse at a junction ATP6 will cause a pulse $\overline{\text{SET}}$ to occur.

Upon the $\overline{\text{SET}}$ signal at time t5 the preconditioned three gate latch arrangement 120 causes the start gate 126 to generate the START pulse. The emergency reset one-shot generator circuit 140 is also actuated to generate the emergency reset pulse Q beginning at time t5.

The $\overline{\text{START}}$ signal on the line 121 sets the derandomizer gate 208 into a logic 0 state to set the latch circuit 170 to produce the sample trigger $\overline{\text{ST}}$ signal. The $\overline{\text{ST}}$ signal actuates the one-shot generator circuit 172 and the delay one-shot generator circuit 178. The circuit 178, in turn, actuates the hold one-shot generator circuit 182. At substantially time t5 these generators produce the leading edges of the $\overline{\text{SAMPLE}}$ signal, the internal unblank delay IUD signal, the $\overline{\text{HOLD}}$ signal, the $\overline{\text{DUMP}}$ signal and the $\overline{\text{DERAN}}$ signal.

The $\overline{\text{DERAN}}$ signal resets the derandomizer gate 208 to a logic one state which prevents subsequent START pulses on the line 121 from setting the latch after expiration of the first START pulse.

At time t6 the $\overline{\text{SET}}$ pulse returns to a logic one state due to the expiration of the 35 nanosecond trigger pulse from the one-shot generator circuit 116. This conditions the start gate 126 to be reset to a logic 0 state after the 0.33 microsecond $\overline{\text{SAMPLE}}$ pulse has returned to a logic one state.

Thus, at point t6 the $\overline{\text{SAMPLE}}$ pulse is rendering the sample and hold circuits 74 able to accept new data. The $\overline{\text{DUMP}}$ signal on the line 96 is being communicated to the sample and hold circuits 74 for preventing them from dumping the new data. The peak detector gate $\overline{\text{PDG}}$ signal has expired, meaning that new data has entered the peak detector circuits 70. The dump peak detector signal $\overline{\text{DPD}}$ is in a logic one state which allows the peak detectors 70 to couple the new data to the summing and ratio circuit 72 and to the sample and hold circuit 74.

Time t7 is approximately 1.5 microseconds after the occurrence of the first pulse present PP pulse. At time t7 a second pulse present PP pulse is shown to occur which brings the derandomizing aspect of the invention into play. Because approximately 3 microseconds is required to process each data pulse, and the subsequent data pulse has occurred only 1.5 microseconds after the first pulse, the derandomizing circuitry allows the subsequent pulse to be stored until able to be processed for later display, rather than being ignored as in previous circuits.

At time t8 the pulse present delayed PP pulse and the PHA pulse from the pulse-height analyzer circuit 32 return to their logic 0 states, conditioned to be regenerated by a second set of data pulses.

At time t9 the 0.33 microsecond $\overline{\text{SAMPLE}}$ pulse returns to a logic one state which causes the START signal to return to a logic 0 state due to resetting of the start gate 126. When the START signal returns to the logic 0 state, the timing one-shot circuit 154 is actuated for resetting the latch 152. This causes the dump peak detector pulse $\overline{\text{DPD}}$ to return to a logic 0 state. Also the transition of the START signal to a logic 0 resets the latch circuit 170 in a holding state. This produces the sample trigger $\overline{\text{ST}}$ signal to have a logic one state and prevents further START signals from actuating the generator circuits 172, 178, 182 until the expiration of the approximate 3 microsecond time corresponding to the $\overline{\text{HOLD}}$ signal and the dump delay $\overline{\text{DD}}$ signal as determined by the $\overline{\text{DERAN}}$ signal.

At time t10 the pulse present PP pulse has returned to the logic 0 state which initiates a new cycle.

At time t11 the pulse present delay signal PPD is generated in response to the pulse present PP signal. The pulse present delayed PPD signal resets the latch 152, generating the respective leading edges of the dump peak detector $\overline{\text{DPD}}$ pulse and the peak detector gate $\overline{\text{PDG}}$ pulse. The second set of data is thus allowed to enter the peak detectors 70 at time t11.

At time t12 the second PHA pulse arrives at the isotope analyzer circuit 94. At time t13 the internal unblank delay signal IUD from the delay one-shot generator circuit 178 returns to a logic one state and actuates the unblank one-shot generator 180. This produces the 1.75 microsecond internal unblank IU signal on the line 99 to the display system 16.

At time t14 the peak detector gate signal $\overline{\text{PDG}}$ is generated in response to the second pulse present delayed PPD signal returning to a logic zero state. This prevents the entry of any other data into the peak detectors 70.

At time t15 the gate 100 generates a second $\overline{\text{SET}}$ pulse as a result of the second set of data pulses. The second $\overline{\text{SET}}$ pulse causes the start gate 126 to generate a second START pulse which is communicated to the latch circuit 170 and to the derandomizer gate 208. This second START pulse, however, is ineffective to reset the latch circuit 170 because the $\overline{\text{DERAN}}$ signal on the line 210 maintains the derandomizer gate 208 in a logic one state. The $\overline{\text{SET}}$ pulse returns to a logic one state at time t16, with the START signal being maintained in a high state for resetting the latch 170 at the expiration of the approximate three microsecond period required for display of the previous data.

At time t17 the second PHA pulse corresponding to the second set of data pulses which have been read into the peak detectors 70 returns to a logic zero state.

At time t18 the internal unblank IU signal provided to the display system 16 for displaying the first set of data, expires. As a feature of the invention, the $\overline{\text{DUMP}}$ pulse is maintained in a logic one state for allowing the first set of data to be coupled to the display system 16 for a period after expiration of the internal unblank IU signal. This assures that data is being coupled to the display for a selected period following the internal unblank IU signal. This added time allows the display system to fully discharge or "bleed."

At time t19 the hold one-shot generator circuit 182 times out to cause the $\overline{\text{HOLD}}$ signal to return to a logic one state. This causes the delay one-shot generator circuit 184 to be actuated for producing the dump delay $\overline{\text{DD}}$ signal and for resetting the output latch circuit 186 for terminating the $\overline{\text{DUMP}}$ signal on the line 198.

At time t20 which is approximately 0.2 microseconds after time t19, the dump delay $\overline{\text{DD}}$ signal expires which is the end of the approximate 3.0 microsecond period during which derandomization is required. The expiration of the dump delay $\overline{\text{DD}}$ pulse causes the $\overline{\text{DERAN}}$ pulse to return to a logic one which allows the derandomizer gate 208 to be reset in response to the START pulse which is being maintained on the line 121.

Because the derandomizer gate 208 has been reset by the end of the approximate 3.0 microsecond period required for processing the first set of data pulses, the START signal corresponding to the second set of data pulses is able to reset the latch circuit 170. This produces the sample trigger $\overline{\text{ST}}$ signal to the one-shot generators 172, 178 which initiate the leading edge of the $\overline{\text{SAMPLE}}$ pulse on the line 97, the IU delay IUD pulse, and the $\overline{\text{HOLD}}$ pulse. The $\overline{\text{HOLD}}$ pulse causes charging of the capacitor 150 through the diode 200 for causing the $\overline{\text{DERAN}}$ signal to return to a logic 0 state. This conditions the derandomizer gate 208 to be nonresponsive to subsequent START pulses on the line 121.

Generation of the second $\overline{\text{SAMPLE}}$ pulse resets the output latch circuit 186 and causes the $\overline{\text{DUMP}}$ signal to go to a logic one state at time t21. This allows the second set of data previously stored in the peak detectors to be coupled into the sample and hold circuits 74 and coupled to the display system 16 for display.

At time t22 the second $\overline{\text{SAMPLE}}$ signal returns to a logic one state which resets the start gate 126 for terminating the second START pulse. This actuates the time one-shot circuit 154 to terminate the dump peak detector $\overline{\text{DPD}}$ pulse for dumping the second set of data from the peak detectors 70. Termination of the START pulse resets the latch 170, for providing the sample trigger signal $\overline{\text{ST}}$ in a logic one state until the expiration of the 3 microsecond data processing time period when another set of data pulses may cause it to initiate another cycle of actuating the generators 172, 178, 182.

At time t25 the six microsecond Q pulse from the emergency reset generator circuit 140 returns to a logic zero state for reinitializing the three gate latch 120 in case a previous $\overline{\text{SAMPLE}}$ signal did not.

As will be understood from the foregoing, even though three microseconds is required to process and display data pulses the derandomizer circuitry allows pulses separated by as little as 1.5 microseconds to be processed without data loss.

THE PEAK DETECTOR 70

Figure 9:
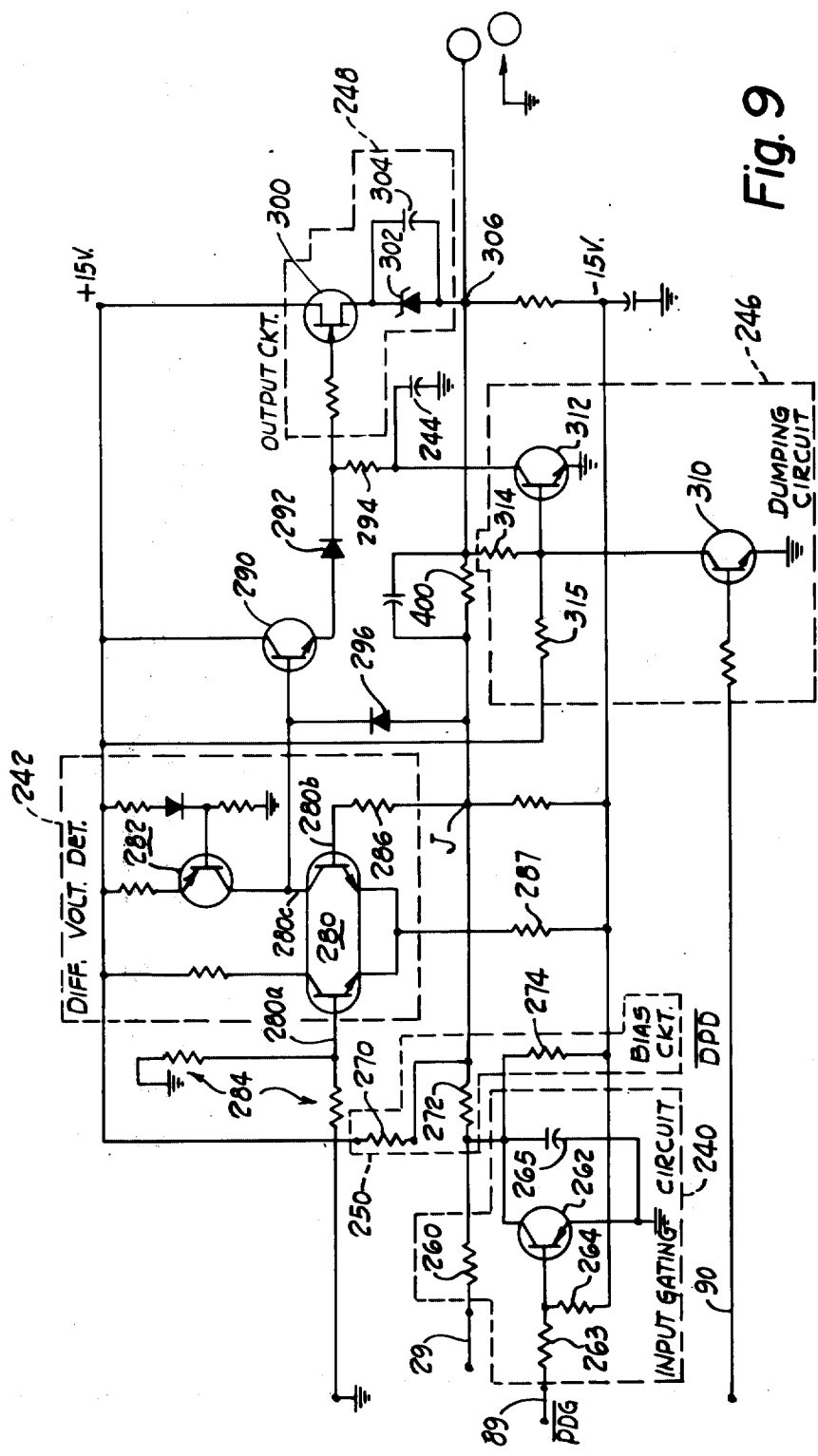
FIG. 9 is a circuit schematic of a novel peak detector used in the signal processor of FIG. 1; and, FIG. 10 is a circuit schematic of a flag generator circuit utilized in the control circuit of FIG. 3.

Referring now to FIG. 9, a preferred peak detector 70 is schematically shown. The illustrated embodiment provides an extraordinarily rapid response time to enable peak detecting of the data pulses having relatively narrow pulse widths. The circuit features selective pulse gating so that only the portion of the data pulse containing the peak is input into the circuit, allowing up to 0.5 microseconds additional processing time for the signal processing circuitry 34. The illustrated circuit also features discharging of internal data storage at a rate proportional to the output signal from the peak detector circuit 70. This further increases circuit response. Additionally the circuit features data signal biasing for biasing the input data pulses to an extremely linear region of operation of the peak detector and for increasing detector selectively by increasing the relative differences between the presence and absence of a data pulse.

The illustrated embodiment of the peak detector 70 is inverting. For data input pulses varying from substantially zero magnitude to a larger negative magnitude, the output pulses vary from substantially zero volts to an increasingly positive magnitude.

The peak detector circuit 70 includes an input gating circuit 240, a differential voltage detector circuit 242, a storage medium in the form of a holding capacitor 244, a dumping circuit 246, an output circuit 248, and a pedestal bias circuit 250.

The input gating circuit 240 is coupled to the pulse-shaping and delay circuitry 30 via the data input line 29 and to the control timing circuit 36 via the line 89. Pulse data on the line 29 is selectively inhibited by the input gating circuit 240 in response to the peak detector gating pulses $\overline{PDG}$ on the line 89. Input of data pulses is normally inhibited by the circuit 240, and the occurrence of a $\overline{PDG}$ pulse inactivates the gate to allow passage of the data signals.

The input gating circuit 240 includes a limiting resistor 260 serially coupled in the input line 29, and a gating transistor 262 having its collector-emitter path coupled between the limiting resistor 260 and circuit ground. An input resistor 263 and a bias resistor 264 are connected to the base of the gating transistor 262 for respectively coupling the base to the line 89 and to a first reference potential of minus 15 volts. A smoothing capacitor 265 is provided coupling the limiting resistor 260 to circuit ground for smoothing the input voltage to the differential voltage detector circuit 242 when the gating transistor 262 changes states. This prevents a sharp voltage increase which would otherwise occur when a data pulse input on the line 89 is suddenly coupled to the detector circuit 42.

In operation a data input pulse appearing on the line 29 is gated to circuit ground through the gating transistor 262 until the occurrence of a $\overline{PDG}$ signal. The $\overline{PDG}$ signal is timed to occur to allow only the peak containing portion of the data input pulse to be coupled to the circuit 242. The −15 volt potential applied to the bias resistor 264 maintains the transistor 262 in a conductive state until the occurrence of the $\overline{PDG}$ signal. It is then rendered nonconductive, allowing passage of the data input pulses.

The pedestal bias circuit 250 is a feature of the invention which generates a voltage to the differential voltage detector circuit 242 in the absence of an input data pulse for causing the output circuit 248 to produce a lower than normal reference voltage level. This produces an effective increase in the magnitude of the data input pulse detected by the differential voltage detector circuit 242, increasing detection selectivity.

The pedestal bias circuit 250 comprises an injector resistor 270, a switching resistor 272, and a loading resistor 274. The injector resistor 270 is coupled between a second reference potential of +15 volts and a junction point J. The switching resistor 272 serially connects the limiting resistor 260 to the junction point J. The loading resistor 274 connects the common junction of the limiting resistor and the switching resistor to the first reference potential of minus 15 volts.

In operation, the bias circuit 250 causes approximately ½ milliamp of current to be inserted into the junction point J when the gating transistor 262 is conductive. This generates a voltage at the junction J which produces a minus 0.8 volts at the output terminal of the detector circuit 70. When the transistor 262 is rendered nonconductive, the loading resistor 274 draws approximately ½ milliamp from the junction J. This ½ milliamp cancels the ½ milliamp injected by the injector resistor 270 and allows the voltage output from the detector circuit 70 to be indicative of the data input voltage on the line 29.

The differential voltage detector circuit 242 is coupled to the input gating circuit 240 for receiving the analog data pulses when the $\overline{PDG}$ signal resides in a logic 1 state. The circuit 242 causes the holding capacitor 244 to be charged to a value corresponding to the peak of the analog data pulse on the line 29.

The differential voltage detector circuit 242 includes a conventional differential transistor pair 280 having a reference input, a signal input, and a signal output terminal, 280a–c, respectively. A current source transistor 282 is coupled to the output terminal 280c and a pair of bias resistors 284 couple the reference input terminal 280a to circuit ground for establishing a reference potential. An input resistor 286 couples the signal input terminal 280b of the differential transistor pair 280 to the junction point J. A second bias resistor 287 is coupled to the differential transistor pair 280 and to the first reference potential of minus 15 volts. The output terminal 280c produces a voltage signal which is indicative of the voltage potential of the junction J exceeding a reference potential determined by the reference input 280a of the differential transistor pair 280.

An emitter-follower transistor 290, a blocking diode 292 and a current limiting resistor 294 are serially coupled between the output terminal 280c and the holding capacitor 244. The emitter-follower transistor 290 has its base terminal connected to the common junction J by an antisaturation diode 296. The collector-emitter path of the emitter-follower transistor 290 selectively couples the second reference potential of 15 volts to the blocking diode 292.

The emitter-follower transistor 290, the blocking diode 292, and the diode 296 advantageously allow the output circuit 248 and the holding capacitor 244 to rapidly respond to changes in the data input signal. The emitter-follower transistor 290 is provided with no D.C. bias so that no current flows through its collector-emitter path except when a data pulse is input during the peak detect mode; i.e., when the peak detector gate $\overline{PDG}$ signal is a logic one. Upon the detection of a data pulse during this time, the transistor 290 is rendered conductive to couple the entire 15 volts from the second reference potential through the blocking diode 292 to the holding capacitor 244. This effective current gain charges the holding capacitor 244 sufficiently fast to enable peak detection of only a 0.5 microsecond input pulse.

Another advantage rendered by the emitter-follower transistor 290 is the voltage isolation it provides for isolating the anode of the blocking diode 292 from a rather large voltage swing produced during operation of the voltage detector circuit 242. Because a capacitance divider effect exists between the blocking diode 292 and the holding capacitor 244, a voltage would be induced across the holding capacitor 244, thereby causing an undesirable glitch in the output signal at the output junction 306. Even though the blocking diode 292 is chosen to minimize capacitance, it has some inherent capacitance which would otherwise cause its anode to vary with the approximate 15 volt swing of the output terminal 280c. By utilizing the emitter-follower transistor 290, however, another back biased diode, the emitter-base junction of the transistor 290, is provided between the blocking diode 292 and the output terminal 280c. This minimizes the voltage induced across the holding capacitor 244 and thus minimizes any output glitch in the output voltage.

The output circuit 248 produces output data pulses having values corresponding to the amount of charge on the holding capacitor 244. This amount of charge is indicative of the amplitude of the data pulses on the input line 29.

The output circuit 248 includes an output transistor 300, a Zener diode 302 connected to the transistor 300, and a smoothing capacitor 304 coupled across the Zener diode 302. The output transistor 300 is a field effect transistor having its gate terminal resistively coupled to the blocking diode 292. The output transistor 300 has its drain terminal connected to the second reference potential and has its source terminal commonly connected to the Zener diode 302 and to the bypass capacitor 304. An output junction 306 is provided at the anode of the Zener diode 302 which is resistively coupled to the first reference potential. A feedback resistor 400 provides a closed loop response between circuits 242 and 248 which realizes extremely linear tracking of the output voltage and the input voltage peak.

The dumping circuit 246 is coupled to the output junction 306, to the holding capacitor 244, and to the line 90 from the control timing circuit 36. The dumping circuit 246 is an important feature of the peak detector as it discharges the holding capacitor 244 at a rate which is determined by the value of the output data pulse at the output junction 306.

The dumping circuit 246 includes an input transistor 310, a dump transistor 312, and a proportional dump resistor 314. The dump transistor 312 has its collector-emitter path respectively connected between the holding capacitor 244 and circuit ground. The dump transistor 312 has its base terminal selectively coupled to circuit ground by the collector-emitter path of the input transistor 310 and resistively connected to the output junction 306 by the proportional dump resistor 314. A bias resistor 315 is coupled to the second reference potential for establishing a D.C. bias voltage on the base of the dump transistor 312.

In operation, the input transistor 310 is normally conductive and clamps the base of the dump transistor 312 low. This renders the dump transistor 312 nonconductive and maintains any charge on the storage capacitor 244. Upon a logic 0 state of the dump peak detector $\overline{DPD}$ pulse on the line 90, the input transistor 310 is rendered nonconductive which causes the dump transistor 312 to become conductive. The charge stored on the holding capacitor 244 begins discharging through the collector-emitter path of the dump transistor 312 at a rate determined by the magnitude of the output voltage at the junction 306. More specifically the magnitude of the voltage at the junction 306 provides a bias through the dump resistor 314 which determines the degree of conductivity of the dump transistor 312. A large output voltage is indicative of a large stored charge on the capacitor 244 and produces a large bias voltage on the junction 306 is indicative of a low store of charge on the capacitor 244, and the transistor 312 receives relatively low base drive through the dump resistor 314.

Referring to the waveforms of FIG. 8, the operation of the peak detector circuit 70 is as follows. An input data signal on the line 29 is coupled to the limiting resistor 260 immediately prior to time $t2$. At time $t3$ the peak detector gate $\overline{PDG}$ and the dump peak detector $\overline{DPD}$ signals are respectively coupled to the input gating circuit 240 and to the dumping circuit 246. The peak detector gate signal times out at a time prior to the time $t5$, rendering the input gating transistor 262 nonconductive. The peak of the data pulse occurs within the interval and is coupled to the junction point J for input into the differential voltage detector circuit 242. This causes a signal to be produced on the output termianl 280c which charges the holding capacitor 244 through the emitter-follower transistor 290. Because the dumping circuit 246 is inactivated, the output circuit 248 produces an output signal on the output junction 306 indicative of the peak of the data signal.

At a time immediately prior to time $t5$, the peak detector gate signal returns to a logic zero state, rendering the input gating transistor 262 conductive. This causes the pedestal bias circuit 250 to inject current into the junction point J via the injector resistor 270 instead of through the switching and loading resistors 272, 274. This causes an output voltage on the order of minus 1 volt to be generated at the output junction 306 when $\overline{DPD}$ is logical O.

At the time $t9$ the dump peak detector pulse $\overline{DPD}$ returns to a logic zero state which actuates the dumping circuit 246. The input transistor 310 is rendered nonconductive which allows the output junction 306 to render the dump transistor 312 conductive for discharging the holding capacitor 244.

THE DUAL ISOTOPE AND THE EXTERNAL CONTROL CIRCUITS

A feature of the control timing circuit 36 is its facility to accommodate dual isotope scanning system and to accommodate display systems 16 of the type which produce control signals for controlling the input of data into the display systems 16. As shown in FIG. 3, a flag generator circuit 222 is provided for interconnection with the sample and hold control generator 96 and with the peak detector derandomizer circuit 92 for accommodating dual isotope operation. A flag switch circuit 224 is coupled to the flag generator circuit 222 and to the display system 16 for producing a pair of output flag signals indicative of the isotope channel selected. The flag switch circuit 224 is controlled so that the output flag signals are either the flag signals generated by the flag generator circuit 222 or are flag signals generated by the display system 16, such as by a tape recorder. The output flag signals produced by the flag switch circuit 224 are also coupled to the sample and hold control generator 96 for controlling generation of the internal unblank IU signal on the line 35.

Figure 10:
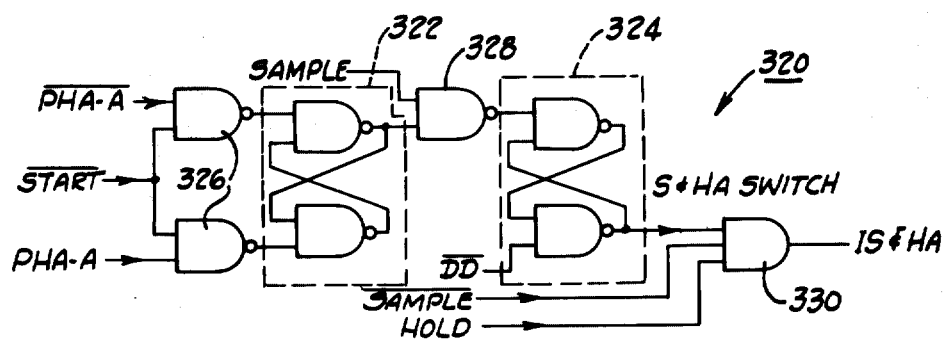

The flag generator circuit 222 is shown in detail in FIG. 10. It comprises a pair of identical logic circuits 320 which respectively produce internal flag signals, IS & HA and IS & HB, representing the particular isotope channel which has been selected for data processing. Because the logic circuits 320 are similar, with one logic circuit being responsive to an A PHA signal channel from one pulse-height analyzer 32 to produce internal IS & HA signals while the other logic circuit is responsive to a B channel PHA signal from another pulse-height analyzer to produce the internal IS & HB flag signals, only the PHA-A logic circuit 320 is shown in FIG. 10.

The logic circuit 320 comprises a storing latch 322 and a switching latch 324. A pair of latch setting gates 326 are responsive to the PHA-A and $\overline{\text{PHA-A}}$ signals and to the START signal for generating signals which determine the state of the storing latch 322. A latch setting gate 328 is coupled to the storing latch 322 and is responsive to the SAMPLE signal for setting the state of the switch latch 324. The switching latch 324 is responsive to and reset by the dump delay $\overline{\text{DD}}$ signal and produces an S & HA switch signal which is indicative of the isotope channel of the data in the signal processing circuitry 34. An output gate 330 is provided responsive to the S & HA switch signal, to the $\overline{\text{SAMPLE}}$ signal and to the $\overline{\text{HOLD}}$ signal for producing the internal IS & HA flag signal. The IS & HA flag signal is indicative of both the isotope channel of the data being processed and the duration during which the data is being communicated from the sample and hold circuit 74 to the display system 16.

In operation the logic circuit 320 is responsive to the PHA-A commands for setting the state of the storing latch 322 to indicate whether the A or B isotope has been selected. When the sample signal goes high, the information is passed to the switching latch 324, setting its state. Because the SAMPLE signal occurs only upon an event being detected by the pulse-height analyzer 32, the switching latch 324 is set only by the occurrence of a valid event.

The switching latch 324 produces an enable signal to the output gate 330 which produces the IS & HA flag signal when an event is in the A window. The period of the IS & HA flag signal corresponds to the period of the HOLD signal less the period of the $\overline{\text{SAMPLE}}$ signal.

The flag switch circuit 224 is responsive to the IS & HA and IS & HB flag signals from the flag generator circuit 222, to the enable isotope A command signal on the line 106, and to the control signals, AFL PLAYBACK, BFL PLAYBACK, from the display signal 16. The flag switch circuit 224 is a conventional logic circuit which is of any suitable design for providing the following logic functions. Upon a logic one state of a $\overline{\text{DIG}}$ signal from the display system 16, the IS & HA signal is passed as the $\overline{\text{S & HA}}$ flag output signal, and the IS & HB signal is passed as the $\overline{\text{S & HB}}$ flag output signal. The S & HA flag signal is a preferred signal and upon its occurrence the $\overline{\text{S & HB}}$ flag signal is automatically inhibited. Therefore, if an event is in both the A and in the B windows as determined by the pulse-height analyzers 32, the data in the signal processing circuitry 34 is treated as A isotope data only. This is accomplished by the ENABLE ISOTOPE A signal on the line 106. The flag switch circuit 224 generates an $\overline{\text{S & HB}}$ IO signal which is indicative of an event occurring in the B window. This signal is not overridden by the preferred S & HA flag output signal so that the occurrence of data in both windows is indicated by the S & HB IO signal and the S & HA signal.

The $\overline{\text{S & HA}}$ and $\overline{\text{S & HB}}$ flag signals are coupled to a gate 332 in the sample and hold control generator 96 (shown in FIG. 7) for enabling the internal unblank IU signal.

Upon a logic zero state of the $\overline{\text{DIG}}$ signal from the display system 16, the AFL PLAYBACK and the BFL PLAYBACK signals from the display system 16 are gated as the $\overline{\text{S & HA}}$ and the $\overline{\text{S & HB}}$ flag output signals respectively. This allows the display system 16 to control generation of the internal unblank signal and any other circuitry depending upon the output flag information.

It will thus be appreciated that a new and improved nuclear radiation, data processing system has been described. Even though some three microseconds may be required for processing data signals, input signals having only a 1.5 microsecond separation may be processed without data loss. Although single order derandomizing circuitry is shown in the data processor for minimizing pulse pile-up, it is understood that additional orders of derandomization are readily accomplished. The addition of the appropriate number of serially connected sample and hold circuits 74 operated by a control circuit in accordance with the foregoing description provides a higher order of derandomization.

Additionally, the derandomizing data processing circuitry advantageously utilizes sample and hold, peak detector circuits, and control circuits which are easily adaptable to accommodate multi-isotope scanning systems and to accomodate special display systems which generate their own timing signals for the input of data. The derandomizing data processing circuitry also features an automatic reset mechanism which automatically resets the entire system if, for any reason, the system latches into an inoperative state due to any unexpected disturbance. The derandomizing data processing circuitry also features a novel peak detector circuit which provides untrafast response time to allow rapid data processing.

Although the invention has been described in its preferred form with a certain degree of particularity, it is understood that the disclosure has been made only by way of example. Changes in the details of construction and the combination and arrangement of parts will be apparent without departing from the spirit and the scope of the invention as claimed.

What is claimed is:

1. A radiation imaging system for examining a radiating body, comprising:
    a. a radiation detector for generating a series of analog radiation representing event signals randomly occurring in time in response to impinging radiation, the event signals representing the spatial locations of said impinging radiation,
    b. a display system for operating on each of a sequence of analog data signals, the operation on each signal requiring a predetermined time for the display system, said display system providing a display representing the spatial distribution of the impinging radiation; and,
    c. a data processor responsive to the randomly occurring event signals for producing the data signals, the data processor including:
        i. at least a first upstream component serially coupled to a second downstream component, each component being capable of at least storing a signal at least corresponding to an event signal, and
        ii. control circuitry connected to the first and second components for advancing a stored signal from said first component toward said second component as a function of the presence of a signal in one of the downstream components and the display system, and for preventing the obliteration of a signal in said first component prior to its transfer toward said second component.

2. The radiation imaging system according to claim 1 wherein the most downstream of said components emitting the date signals to the display system.

3. The radiation imaging system according to claim 2 and further including control means for selectively inhibiting signal input to the first component as a function of said predetermined time.

4. The radiation imaging system according to claim 3 wherein the first component is a peak detector circuit and the second component is a sample and hold circuit.

5. A nuclear radiation imaging system for clinically examining an irradiated body, comprising:
 a. a radiation detector for generating a series of randomly occurring sets of analog event signals in response to impinging radiation; and,
 b. a data processor responsive to the sets of event signals for producing a sequence of analog data pulses having pulse width corresponding to at least a minimum period of time, the data processing means including:
  i. a front end processor responsive to the sets of event signals for producing a sequence of sets of position pulses representing positional information of the radiation which impinges on the detector means, and
  ii. a back end processor responsive to successive sets of position pulses for providing the sequence of analog data pulses, the back end processor including at least two sets of components respectively series coupled in cascade for at least selectively receiving and temporarily storing successive sets of coordinate pulses and control circuitry for advancing a set of coordinate pulses from one set of components to another in response to another set of components being in condition to accept said coordinate pulses without thereby causing loss of information borne by other sets of coordinate pulses.

6. The radiation imaging system according to claim 5 wherein said control circuit controls the input and passing along of the sets of position pulses between the storage components as a function of the beginning of the minimum period of time.

7. The radiation imaging system according to claim 5 wherein the data processing means includes:
 a. a dual isotope pulse analyzer for characterizing the analog event pulses which are produced in response to impinging radiation from at least two isotopes; and
 b. a control unit for conditioning the back end processor to be responsive to a selected one of the sets of analog event signals.

8. In a nuclear radiation imaging system for clinically inspecting an irradiated body, the method of derandomizing randomly occurring data pulses representative of the nuclear radiation emitted from the body comprising the steps of:
 a. sequentially inputting a first data pulse into the first of a plurality of serially connected cascade coupled storage units;
 b. marching the data pulse through said serially connected storage units to the last in sequence storage unit with a timing which is a function of the presence of other data pulses in the storage units;
 c. outputting and maintaining the output of the data pulse from the last in sequence storage unit upon the occurrence of a predetermined event; and,
 d. selectively inputting a subsequent data pulse into the second from last in sequence storage unit only upon the occurence of a condition of the predetermined event.

9. The method of derandomizing data pulses according to claim 8 wherein the predetermined event is the expiration of a preselected time period.

10. The method of derandomizing data pulses according to claim 9 wherein the condition is the beginning of the preselected time period.

11. The method of derandomizing according to claim 8 wherein the predetermined event is the expiration of a control pulse from associated equipment.

12. The method of derandomizing according to claim 8 wherein the step of sequentially inputting includes the step of selecting a data pulse from a preselected one of several data input channels.

13. The method of derandomizing according to claim 8 wherein the step of inputting comprises the step of inputting a data pulse from any of several data input channels.

14. A nuclear radiation imaging system for clinically examining a body comprising:
 a. radiation detector means for generating a series of sets of analog event signals in response to impinging nuclear radiation;
 b. data processing means responsive to the sets of event signals for producing a sequence of analog data pulses having at least a minimum period of time between leading edges of successive pulses, the data processing means including a plurality of data storage cells for storing in sequence a succession of the sets of analog event signals;
 c. a control unit coupled to the data processing means for controlling pulse input into and pulse output from the plurality of data storage cells, the control unit having internal input means responsive to the occurrence of the event signal for initiating a data processing sequence by the data processing means, and further having external input means for selectively interrupting the data processing sequence for lengthened minimum time separation.

15. The nuclear radiation imaging system according to claim 14 wherein:
 a. the radiation detection means includes dual isotope discriminating means for characterizing first and second sets of analog event signals, and
 b. said control unit conditions the data processing means to be responsive to a select one set of analog event signals.

16. The nuclear radiation imaging system according to claim 14 wherein the control unit includes emergency reset means for automatically conditioning the data processing means to accept a new set of pulses upon the expiration of a predetermined period of time, thereby assuring that the data processing means does not become set into an inoperative, nondata processing state.

17. A nuclear radiation imaging system for clinically examining an irradiated body, comprising:
 a. radiation detection means for generating a series of sets of analog event signals in response to impinging radiation; and
 b. data processor means responsive to the said event signals for producing a sequence of analog data pulses having pulse width corresponding to at least a minimum period of time, the data processing means including:
  i. a front end processor responsive to the sets of event signals for producing a sequence of sets of position pulses representing positional information of the radiation which impinges on the detector means, and
  ii. a back end processor responsive to succcessive sets of position pulses for providing the sequence of analog data pulses, the back end processor including a plurality of sets of storage cells respectively coupled in cascade for selectively receiving and temporarily storing successive sets of coordinate pulses in timed relation to the minimum period of time, said back end processor including a control unit for controlling the input and passing along of sets of position pulses between the storage cells as a function of the beginning of the minimum period of time, said control unit including emergency reset means for automatically resetting the control unit upon the expiration of a predetermined period of time, thereby assuring that the back end processor does not inadvertently become set into an inactive, nondata processing state.

18. A nuclear radiation imaging sytem for clinically examining an irradiated body, comprising:
  a. radiation detection means for generating a series of sets of analog event signals in response to impinging radiation; and
  b. data processor means responsive to the said event signals for producing a sequence of analog data pulses having pulse width corresponding to at least a minimum period of time, the data processing means including:
    i. a front end processor responsive to the sets of event signals for producing a sequence of sets of position pulses representing positional information of the radiation which impinges on the detector means, and
    ii. a back end processor responsive to successive sets of position pulses for providing the sequence of analog data pulses, the back end processor including a plurality of sets of storage cells respectively coupled in cascade for selectively receiving and temporarily storing succcessive sets of coordinate pulses in timed relation to the minimum period of time, said back end processor including a control unit for controlling the input and passing along of sets of position pulses between the storage cells as a function of the beginning of the minimum period of time, said control unit including first input means responsive to the occurrence of an event signal for initiating a data processing sequence in the back end processor, said system further comprising:
  c. external input means for inputting an externally generated control signal for interrupting and delaying the data processing cycle and thereby effectively lengthening the minimum time of duration.

19. A nuclear radiation imaging system for clinically examining a body, said system comprising:
  a. at least first and second radiation discriminators for generating first and second series of sets of analog event signals in response to impinging radiation;
  b. data processing means coupled to the radiation detectors for producing a sequence of analog data pulses, each having pulse width corresponding to at least a minimum period of time, the data processing means including a plurality of data storage cells which successively store and transmit in sequence sets of signals representative of the situs of the impinging radiation; and,
  c. a control unit for selectively conditioning the data processing means to be responsive to either a select one set of the analog event signals or to both the first and second sets of analog event signals said control unit including an emergency reset mechanism for automatically conditioning the data processing means to accept a set of new signals after the expiration of the predetermined period of time to thereby assure that the data processing means does not become set and locked into an inoperative nondata processing state.

20. The system according to claim 19, wherein the control unit further includes an external input mechanism responsive to externally supplied signals for selectively inhibiting the data processing means and increasing the minimum time separation between individual pulses.

21. A method of derandomizing the sequence of analog event pulses having peak magnitudes of presenting data in a scintillation camera system to produce data pulses having a pulse width corresponding to a minimum predetermined period of time, comprising the steps of:
  a. peak detecting only the portion of the event pulse comprising the peak;
  b. storing in input storage and generating a voltage representation of said peak until after the expiration of a first said predetermined period;
  c. sampling, storing in an output storage, and providing the voltage representation as the data pulse to initiate a second said predetermined period, comprising communicating said event pulse to said input store and gating the event pulse into the input store a predetermined delay after arrival;
  d. maintaining the data pulse through the second predetermined period;
  e. discharging said first storage;
  f. peak detecting and storing in the input storage the peak containing portion of a subsequently occurring event pulse until the completion of said second predetermined period, and
  g. wherein the communicating step comprises communicating the subsequent event pulse to the output storage, the end of the first predetermined period to initiate the second predetermined period.

22. A peak detector for detecting a peak of a data pulse comprising:
  a. differential voltage detection means having a first input coupled to a reference potential and having a second input for receiving data pulses;
  b. input gating means for selectively gating a data pulse to said second input, said input gating means having a first state for communicating said data pulse and having a second state for blocking input of the data pulse;
  c. storage means coupled to said differential voltage detector for storing an amount of charge proportional to the peak of said data pulse;

d. output circuit means coupled to said storage for generating an output voltage proportional to said amount of charge;

e. biasing means coupled to said input gating means and to said second input of said differential voltage detector for supplying bias voltage to said second input during said second state of said input gating means to thereby facilitate operation of said peak detector in a linear operating range, and proportional dumping means coupled to said output circuit means for selectively discharging said storage means at a rate proportional to said output voltage.

23. A peak detector according to claim 22, wherein the storage means comprises a capacitor.

24. The peak detector according to claim 22, wherein said differential voltage detector comprises a differential transistor pair of one conductivity type having a current source transistor coupled thereto of the other conductivity type, and further including an emitter-follower transistor of said one conductivity type coupling said differential transistor pair to said capacitor for increasing the charging rate of the capacitor.

25. The peak detector according to claim 24, further including a blocking diode having its anode coupled to said emitter-follower transistor and its cathode coupled to said capacitor.

26. The peak detector of claim 25 wherein said output circuit means comprises a serial connection of a field effect transistor and a Zener diode.

27. The peak detector according to claim 26, wherein said input gating means includes a gating transistor having its base responsive to said first input gating signal and further comprises a smoothing capacitor coupled across said gating transistor.

28. A method of derandomizing a sequence of analog event pulses having peak magnitudes representing data in a scintillation camera system to produce data pulses having a pulse width corresponding to a minimum predetermined period of time, comprising the steps of:

a. peak detecting only the portion of the event pulse comprising the peak;

b. storing an input storage and generating a voltage representation of said peak until after the expiration of a first said predetermined period;

c. sampling, storing in an output storage, and providing the voltage representation as the data pulse to initiate a second said predetermined period;

d. maintaining the data pulse through the second predetermined period;

e. discharging said first storage; and, f. peak detecting and storing in the input storage the peak containing portion of a subsequently occurring event pulse until the completion of said second predetermined period.

* * * * *